(12) United States Patent  (10) Patent No.: US 9,095,603 B2
Shoseyov  (45) Date of Patent: Aug. 4, 2015

(54) ANTI-ALLERGY COMPOSITIONS

(75) Inventor: Oded Shoseyov, Carmei Yosef (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 1207 days.

(21) Appl. No.: 12/295,968

(22) PCT Filed: Apr. 10, 2007

(86) PCT No.: PCT/IL2007/000450

§ 371 (c)(1),
(2), (4) Date: May 4, 2009

(87) PCT Pub. No.: WO2007/113835

PCT Pub. Date: Oct. 11, 2007

(65) Prior Publication Data

US 2009/0246287 A1  Oct. 1, 2009

Related U.S. Application Data

(60) Provisional application No. 60/789,129, filed on Apr. 5, 2006.

(51) Int. Cl.
| | |
|---|---|
| A61K 45/00 | (2006.01) |
| A61K 47/00 | (2006.01) |
| C08B 15/06 | (2006.01) |
| C07H 1/00 | (2006.01) |
| C07H 3/00 | (2006.01) |
| C08B 37/00 | (2006.01) |
| C12P 19/04 | (2006.01) |
| A61K 31/716 | (2006.01) |

(52) U.S. Cl.
CPC .................................. *A61K 31/716* (2013.01)

(58) Field of Classification Search
None
See application file for complete search history.

(56) References Cited

U.S. PATENT DOCUMENTS

| 6,372,718 B2* | 4/2002 | Santar et al. ............... 514/25 |
| 7,879,340 B2* | 2/2011 | Sanders ................. 424/239.1 |
| 2004/0082907 A1 | 4/2004 | James |
| 2005/0197319 A1 | 9/2005 | Nonomura et al. |
| 2005/0256082 A1 | 11/2005 | Nonomura et al. |
| 2005/0271613 A1 | 12/2005 | Suzuki et al. |

FOREIGN PATENT DOCUMENTS

| EP | 0308147 A1 | 3/1989 |
| EP | 1389466 A1 | 2/2004 |
| WO | 03/015744 A1 | 2/2003 |
| WO | 03/051376 A1 | 6/2003 |
| WO | WO 2004/048519 | * 6/2004 |
| WO | 2004100966 A1 | 11/2004 |

OTHER PUBLICATIONS

Shani et al. 'Oxidized Cellulose Binding to Allergens with a Carbohydrate-Binding Module Attenuates Allergic Reactions.' J Immunol. 186:1240-1247, 2011.*
Kurucz et al. 'Current Animal Models of Bronchial Asthma.' Curr. Pharm. Des. 12:3175-3194, 2006.*
Thomsen et al. 'Atopic Dermatitis: Natural History, Diagnosis, and Treatment.' Hindawi Publishing Corporation ISRN Allergy vol. 2014, Article ID 354250, 7 pages http://dx.doi.org/10.1155/2014/354250.*
International Search Report for PCT/IL2007/000450.
Emberlin et al., A Double Blind, Placebo Controlled Trial of Inert Cellulose Powder for the Relief of Symptoms of Hay Fever in Adults, Feb. 2006, Current Medical Research and Opinion, vol. 22, No. 2, pp. 275-285.
Hamelmann et al., Noninvasive Measurement of Airway Responsiveness in Allergic Mice Using Barometric Plethysmography, 1997, American Journal of Respiratory and Critical Care Medicine, vol. 156, pp. 766-775.
Josling et al., Use of Cellulose Powder for the Treatment of Seasonal Allergic Rhinitis, Jul./Aug. 2003, Advances in Therapy, vol. 20, No. 4, pp. 213-219.
Kirmaz et al., Effects of Glucan Treatment on the Th1/Th2 Balance in Patients With Allergic Rhinitis: A Double-Blind Placebo-Controlled Study, 2005, European Cytokine Network, vol. 16, No. 2, pp. 128-134.
Kumar et al., HNO3/H3PO4-NANO2 Mediated Oxidation of Cellulose—Preparation and Characterization of Bioabsorbable Oxidized Celluloses in High Yields and With Different Levels of Oxidation, 2002, Carbohydrate Polymers, vol. 48, pp. 403-412.
Raftery, Absorbable Haemostatic Materials and Intraperitoneal Adhesion Formation, 1980, British Journal of Surgery, vol. 67, pp. 57-58.
Shirai et al., Epigallocatechin Gallate-Induced Histamine Release in Patients With Green Tea-Induced Asthma, Jul. 1997, Annals of Allergy, Asthma and Immunology, vol. 79, pp. 65-69.
Strong et al., Intranasal Application of Chitin Microparticles Down-Regulates Symptoms of Allergic Hypersensitivity to Dermatophagoides pteronyssinus and *Aspergillus fumigatus* in Murine Models of Allergy, 2002, Clinical and Experimental Allergy, vol. 32, No. 12, pp. 1794-1800.
Zhu et al., Examination of Aqueous Oxidized Cellulose Dispersions as a Potential Drug Carrier: II. In Vitro and In Vivo Evaluation of Phenylpropanolamine Release From Microparticles and Pellets, 2004, AAPS PharmSciTech, vol. 5, No. 4, Article 70, pp. 1-8.
Kumar, V., et al., "Preparation and Characterization of Spray-Dried Oxidized Cellulose Microparticles," Pharmaceutical Development and Technology, 6(3), 449-458 (2001).

* cited by examiner

*Primary Examiner* — Nora Rooney
(74) *Attorney, Agent, or Firm* — Brooks Kushman P.C.

(57) ABSTRACT

The present invention relates to particles of glucans, particularly oxidized cellulosed for use in medicine. The invention further discloses pharmaceutical compositions for the treatment and/or prophylaxis of diseases or disorders associated with or mediated by allergens.

16 Claims, 7 Drawing Sheets

Total cell count day 21

Cell types day 21

Figure 3A Lolium perenne
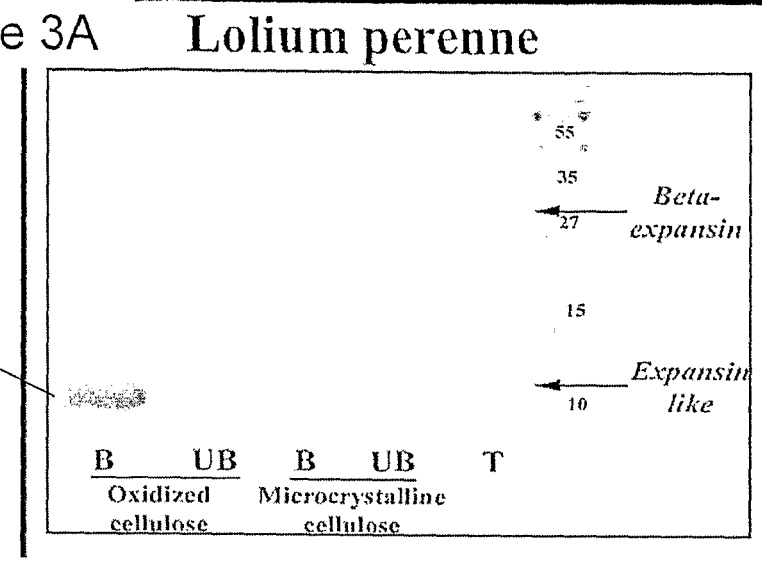
Pollen allergen Lol p 3 (Expansin like)
Figure 3B Lolium rigidum
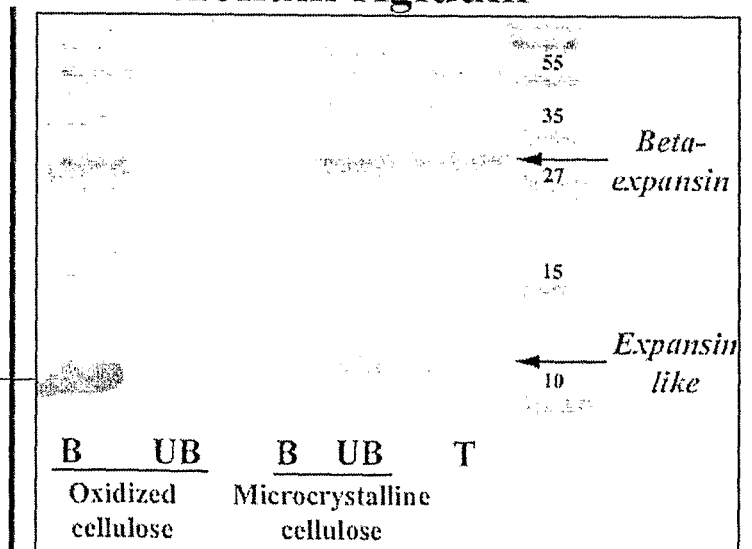
Pollen allergen Lol p 3 (Expansin like)
B=Bound fraction
UB=Unbound fraction
T=Total

- Polysaccharide
- IgE
- Pollen allergen family I
- Pollen allergen family II
- Pollen allergen family III

ANTI-ALLERGY COMPOSITIONS

CROSS-REFERENCE TO RELATED APPLICATION

This application claims the benefit of U.S. provisional application Ser. No. 60/789,129 filed Apr. 5, 2006.

FIELD OF THE INVENTION

This invention relates to methods and compositions for the treatment and/or prevention of allergies.

BACKGROUND OF THE INVENTION

The most powerful and frequent airborne allergens are plant pollens and among these, grass elicits one of the most widely spread forms of plant allergens. Inhaled pollen and especially grass pollen, which contributes to allergic disorders in up to 25% of adults, represents a major cause of type I allergy response in to susceptible individuals. Amongst the allergic responses are allergic rhinitis, conjunctivitis, hives and seasonal asthma. The impact of type I allergy in industrialized countries has increased tremendously, especially in children, and is now becoming a major health problem.

Asthma is the most common chronic disease of the lung which affects between 5 and 15% of the population in the industrial world. It is an inflammatory disease characterized by recurrent attacks of airway obstruction, traditionally treatable by anti-inflammatory drugs, particularly steroids. Despite new treatments, the prevalence and morbidity of asthma have been oil the rise in the last two decades.

Asthma is characterized by two phases that occur after allergen exposure: early asthmatic reaction, EAR, involving early bronchoconstriction that occurs within minutes, and a late asthmatic reaction, LAR, involving subsequent inflammatory reaction of the airways, which occurs 4 to 8 hours later and characterized by thickening of the bronchial walls due to edema and inflammatory cell infiltration of lymphocytes, eosinophils and others. The asthmatic events commence with inhalation of a trigger allergen that is presented to the immune system. A specific IgE-allergen complex which forms, subsequently binds to a specific mast cell membrane receptor (FcεRI), thereby causing degranulation and release of bronchoconstrictors and pro-inflammatory mediators like histamine. As a result the airway smooth muscle contracts and the bronchial lumen becomes narrow, leading to an increase in airway resistance and shortness of breath. This EAR is self-limited and resolves spontaneously within 1 hour or by the use of adrenergic medication. However, after about 4 hours, due to the inflammatory process initiated by the IgE-allergen complex and the release of proinflammatory mediators, the bronchial walls become swollen. This late process (LAR) may be reversed or even preventable by the use of steroids.

Asthma, allergic rhinitis and atopic dermatitis are almost invariably accompanied by elevated levels of IgE. Genetic analyses of families have shown that bronchial hyperresponsiveness (BHR) and IgE levels are linked. Thus, in clinical practice, specific IgE-allergen (as demonstrated by skin testing or in vitro assays) is generally believed to be inextricably connected to the induction of allergic airway symptoms, and is used as a guide for environmental modification and immunotherapy. The interaction of IgE with antigen is known to lead to a variety of immunological sequelae. Cross-linking of IgE bound to mast cells by FcεRI triggers the release of preformed vasoactive mediators, synthesis of prostaglandins and leukotrienes, and the transcription of cytokines (proinflammatory mediators).

The grass allergen of group-I that belong to the β-expansin gene family shares a high degree of amino acid sequence similarity with allergens belonging to different groups, i.e., group II/III, regardless of their origin. Expansins comprise of two closely related families, α-expansins (not glycosylated) and β-expansins (glycosylated). Expansins are secreted cell wall proteins (~26 kDa) and are known to be involved in the loosening of the plant cell wall during plant growth as well as in the fruit softening process. The presence of high levels of expansins in the pollen suggests their involvement in pollen germination and pollen penetration and growth through the pistil.

The expansins are composed of two distinct domains: a C-terminal cellulose binding domain (CBD) and an N-terminal domain that exhibits some sequence similarity with the family of 45 endo-glucanases. The CBD allows expansins to interact with the cellulose microfibrils of the plant cell walls and is known to be the minimal structure required for plant cell-wall expansion and disruption of cellulose fiber-to-fiber interactions. It is important to note that expansins also possess a cystein-proteinase activity that may further explain their abilities to contribute to the allergenic reaction.

Interestingly, the allergens belonging to families II/III are small proteins (~10 kDa) that share ~40% identity and ~60% similarity with the amino acid sequence of the C-terminal (CBD) of the expansins, thus suggesting that the CBD part is the common antigen in these groups of proteins (allergen families I/II/III). A direct support for this observation comes from the presence of the IgE antigen epitopes specifically on the cellulose binding cleft of the CBD domain as known for the rye-grass (*Lolium perenne*), a major group I allergen Lol pI protein. In fact, two of the four predicted T-cell epitopes readily exposed on the surface of the CBD match with IgE-binding regions. Some of these predicted T-cell epitopes are localized in the flattened regions of the beta-sandwich exposing aromatic amino acids that are known to be involved in the recognition of the cellulose by the CBD part of this protein.

A further support for this model is given by the fact that the CBD domain also possesses the classical immunoglobulin-like folding structure known as the common IgE binding site. Furthermore, the Ig-like three-dimensional fold of the CBD of the Lol pI allergen strikingly resembles those of Der f2 and Der p2, the main group 2 of house dust mite allergens.

Tree pollens are major causes of pollinosis and among them olive pollen has high clinical relevance in many areas around the world. A small olive pollen protein, Ole e 10 (10 kDa) is recognized as a major inducer of type I allergy in humans. The ability of Ole e 10 to bind soluble polysaccharides has been known. Ole e 10 binds specifically to 1,3-β-glucans, in addition this protein shows sequence identity with the non-catalytic C-terminal domains of several plant 1,3-β-glucanases (27-53% identity, 44-69% similarity). The change in the secondary structure of Ole e 10 in the presence of laminarin is in agreement with the fact that CBMs appear to have pre-formed carbohydrate recognition sites that mirror the solution conformations of their target sugars. The biochemical activity of Ole e 10 is in agreement with the fact that callose (1,3-β-glucan) is one of the major component of the pollen tube wall. Thus, Ole e 10 could act as a carbohydrate-binding protein that interacts with 1,3-β-glucans during cell wall synthesis/degradation during pollen germination.

Attempts to prevent allergy by employing allergen inactivating agents for inactivating allergens in the environment by specific polysaccharides have been documented. US Patent Applications Nos. 2005/0197319 and 2005/0256082 disclose an allergen inactivating agent containing a polysaccharide having a cellulose ether or a starch ether backbone, which is said to be suitable for inactivation of house dust and other allergens in the environment by forming a non-specific adsorbing matrix.

US Patent Application NO. 2004/0082907 discloses an apparatus for dispensing a restricted amount of powdered materials particularly to the human nasal tract. This device was used by Josling et al (2003) and Emberlin et al (2006) for the intranasal delivery of natural cellulose in the treatment of allergy symptoms from hay fever, dust mites and animal dander. The authors hypothesized that the natural crystalline cellulose reacts with the nasal mucus to create a physical barrier to pollen dust.

Oxidized cellulose has been investigated as immobilizing fabric matrices for various agents such as drugs, enzymes and proteins (Raftery 1980). The release of phenylpropanolamine from an oxidized cellulose derivative of phenylpropanolamine was also investigated as having potential drug celivery properties (Zhu, 2004).

Additionally, microparticles of oxidized cellulose are used for homeostasis.

REFERENCES

[1] US Patent Application No. 2005/0197319.
[2] US Patent Application No. 2005/0256082.
[3] US Patent Application No. 2004/0082907.
[4] Josling P. and Steadman S., Use of cellulose powder for the treatment of seasonal allergic rhinitis. Adv Ther. 2003, 20(4): 213-9.
[5] Emberlin J C. and Lewis R A., A double blind placebo controlled trial of inert cellulose powder for the relief of symptoms of Hay fever in adults. Curr. Med. Res. Opin. 2006, 22(2): 275-85.
[6] Raftery A T., Absorbable haemostatic materials and intraperitoneal adhesion formation. Br. J. Surg. 1980, 67: 57-58.
[7] Zhu L, Kumar V, Banker G S., Examination of Aqueous Oxidized Cellulose Dispersions as a Potential Drug Carrier. II. In Vitro and In Vivo Evaluation of Phenylpropaniolamine Release From Microparticles and Pellets. AAPS PharmaSciTech 2004, 5(4): 1-8.
[8] Kumar V. and Yang T., HNO/HPO-NANO mediated oxidation of cellulose—Preparation and characterization of bioabsorbable oxidized celluloses in high yields and with different levels of oxidation. Carbohydrate Polymers. 2002, 48: 403-12.
[9] Shirai T., Sato A., Chida K., Hayakawa H I., Akiyama J., Iwata M., Taniguchi M., Reshad K. and Hara Y., Epigallocatechin gallate-induced histamine release in patients with green tea-induced asthma. Ann. Allergy Asthma Immunol., 1997, 79: 65-69.
[10] Hamelmann E., Schwarze J., Takeda K., Oshiba A., Larsen G L., Irvin C G., and Gelfand E W., Noninvasive measurement of airway responsiveness in allergic mice using barometric plethysmography. Am. J. Respir. Crit. Care Med., 1997, 156: 766-775.

SUMMARY OF TUE INVENTION

The employment of unmodified cellulose in medicaments for the treatment or prophylaxis of allergic reactions is based on the assumption that the cellulose, or a derivative thereof, can form a physical barrier between the allergen and the tissue on which the cellulose has been applied. Despite the seemingly important advantages of such a prophylactic, the use of non-modified crystalline cellulose may be problematic for numerous reasons.

Plant allergens in general possess natural ability of interaction with specific polysaccharides of the plant cell-wall and thus can specifically recognize and bind to target glucans. Although the natural target glucans for some plant allergen is not clear, it has been established that plant allergens have none or very poor recognition of crystalline cellulose, making interaction with crystalline cellulose substantially impossible. In addition, the observation that cellulose cannot dissolve in bodily tissues and thus cannot be regarded as biodegradable or biocompatible material devoids the use thereof in therapeutically useful applications.

The oxidized cellulose, on the other hand, having an amorphous presentation was found by the inventors of the present invention to have the necessary recognition of and binding properties to various plants allergens. The inventors have successfully determined that particles, e.g., micro or nano in size, of biocompatible polysaccharides such as glucans may serve as broad-spectrum allergen blockers by blocking the IgE epitopes. It is known that the particles, being water-insoluble, can be cleared from the airway by the mucociliary transport. The structural plasticity of the various glucans, and particularly that of oxidized cellulose, on one hand, and the biocompatibility of the glucans, on the other, make this class of compounds an ideal broad-spectrum allergen blocker that may be formulated for administration via inhalation, intranasal application (e.g., as nasal spray), ocular application (e.g., eye drops), topical application (e.g., creams, ointments) and for mucosal application.

Cellulose and oxidized cellulose are different compounds having vastly different chemical and physical properties, despite the fact that the latter may be produced from the former, in terms of their respective chemical structure, reactivity and toxicity. A person skilled in the art would appreciate that when searching for an alternative active agent to commonly used agent, particularly for human and animal use, one needs to tale into account that the alternative substance used in the pharmaceutical product must be toxicologically acceptable, well tolerated by the tissue to which it is applied, (e.g., skin, mucosa, etc.) stable, and inexpensive to produce. In the absence of a clear and predictable relationship to between the action required and the structure of the chemical agent, its toxicological acceptability, tolerance and/or the stability, the search for such suitable alternative that possess the required characteristics is complex. As may be appreciated from the present description, the aim of the present invention was to attain an active compound, an alternative to cellulose, which would be at least as active as commercially available anti-allergic formulations but at the same time be absent of at least some of the numerous drawbacks associated with the use of cellulose as described above.

In its broadest scope, the present invention relates to the use of anti-allergy compounds, particularly glucans for preparing medicaments for therapeutic treatment and/or prophylaxis of various allergen-mediated or associated disease or disorder, to pharmaceutical compositions comprising them and to methods for therapeutic treatment and/or prophylaxis of various allergen-mediated or associated diseases or disorders. The present invention also relates to kits or commercial packages containing any one of the compositions of the invention as particular formulations and dosage forms and instructions for use.

In one aspect of the present invention there is provided a pharmaceutical composition comprising at least one glucan for the treatment and/or prophylaxis of at least one disease or disorder associated with at least one allergen, wherein said at least one glucan is not cellulose or any non-oxidized form thereof. Excluded from the scope of the present invention are any non-oxidized cellulose derivatives including ethers, esters, and alkyls thereof.

The term "glucan" refers to a polysaccharide of sugar monomers linked together by glycosidic bonds. The glucan may be α- or β-glucan and may be of natural, synthetic or semi-synthetic origin. The glucan may also be a combination of two or more glucans. Within the scope of the present invention, the term does not encompass cellulose or any non-oxidized form thereof (i.e., cellulose ethers, cellulose esters, etc.), unless specifically disclosed.

In one embodiment, the glucan employed by any of the methods or compositions of the invention is a polysaccharide associated with the cell walls of pollen and plant pistils of plants.

In another embodiment, the glucan is selected amongst polysaccharides that bind protein allergens.

In another embodiment, the glucan is selected amongst polysaccharides that upon binding to an allergen interfere with IgE interactions.

In yet another embodiment, the glucan is selected amongst polysaccharides having repeating glucose monomers.

In another embodiment, the glucan is selected amongst polysaccharides having a plurality of D-glucose monomers linked together by glycosidic bonds.

In still another embodiment, the glucan is selected from β-1,4-glucans, β-1,3-glucans, β-1,6-glucans, α-1,4-glucans, α-1,6-glucans, β-1,3/β-1-6-glucans, and α-1,4/α-1,6-glucans.

In yet another embodiment, the glucan is selected from oxidized cellulose, pullulan, starch, glycogen, dextran, lichenin, mannan, galactomannan, arabinoxylan, Galacton®, chitosan, chitin and any derivative thereof.

In another embodiment, the glucan is hemicellulose.

In another embodiment, the glucan is different from hemicellulose or cellulose.

The glucans employed in the present invention may be fully oxidized partially oxidized or non-oxidized. As stated above, the glucan, however, is not cellulose or any non-oxidized form thereof.

Non-limiting examples of glucans in accordance with the invention are arabinoxylan, barely beta-glucan, oat beta-glucan Galacton®, pullalan, carob galactomannan, xyloglucan, guar galactomannan, pectic galactan, rhamnogalacturonan-galacturonic acid, pachyman, curdlan, chitin derivatives, chitosan, oxidized cellulose and mannan.

Non-limiting examples of glucans in accordance with the invention are arabinoxylan, barely beta-glucan, oat beta-glucan galacton, pullulan, carob galactomannan, xyloglucan, guar galactomannan, pectic galactan, rhamnogalacturonan-galacturonic acid, pachyman, curdlan, chi tin derivatives, chitosan, oxidized cellulose and mannan.

In another embodiment, the glucan is oxidized cellulose, any salt and derivative thereof as disclosed herein.

The oxidized cellulose independently of its crystallinity or conjugation to another moiety, e.g., drug, as discussed herein, is typically in the form of solid particulates which may be spherical or randomly shaped and which may be micro or nano in size (microparticles and/or nanoparticles). Preferably, the particles of oxidized cellulose have averaged diameters in the range of 0.01 to 100 microns.

Thus, in another aspect of the present invention, there is provided microparticles and/or nanoparticles of oxidized cellulose.

In one embodiment, the microparticles and/or nanoparticles of the oxidized cellulose are suitable for use in medicine.

The invention additionally provides a pharmaceutical composition comprising microparticles and/or nanoparticles of oxidized cellulose, a salt or a derivative thereof.

The terms "microparticles" and "nanoparticles" are used in plural merely to indicate that the compositions of the invention comprise a plurality of such particles and should not be considered to render the singular form uninventive.

In one embodiment, the oxidized cellulose particles have an averaged diameter of between about 0.01 and about 100 microns.

In another embodiment, the oxidized cellulose particles have an averaged diameter of between about 0.01 and about 95, 90, 85, 80, 75, 70, 65, 60, 55, 50, 45, 40, 35 or 30 microns.

In another embodiment, the oxidized cellulose particles lave in averaged diameter of between about 0.1 and about 50 microns.

In yet another embodiment, the oxidized cellulose particles have an averaged diameter of between about 0.1 and about 30 microns.

In still another embodiment, the oxidized cellulose particles have an averaged diameter of between about 0.1 and about 10 microns.

It should be noted that the averaged diameter of the oxidized cellulose particles may be measured by any method known to a person skilled in the art. The term "averaged diameter." refers to the arithmetic mean of measured diameters, wherein the diameters range ±25% of the mean. For example, the expression "averaged diameter of between about 0.01 and about 100 microns" encompasses particles having diameters 25% smaller than 0.01 microns and 25% larger than 00 microns, namely from 0.0075 microns to 125 microns. An averaged diameter of 30 microns thus refers to an actual average of between 22.5 and 37.5 microns.

In another embodiment of the present invention, the composition comprising microparticles and/or nanoparticles of oxidized cellulose is suitable for the treatment and/or prophylaxis of at least one disease or disorder.

In another embodiment, said disease or disorder is associated with or mediated by at least one allergen.

In another aspect of the present invention, there is provided a pharmaceutical composition comprising oxidized Cellulose, a salt or a derivative thereof for the treatment and/or prophylaxis of at least one disease or disorder associated with or mediated by at least one allergen.

As known to a person skilled in the art, "Oxidized cellulose" is a rigid, unbranched, long chain polymer, consisting of 3,000 to 5,000 glucose residues in β-(1,4) linkage, having at least part or all of the hydroxymethylene (exocyclic —$CH_2OH$) groups oxidized to carboxylic acid (—COOH) groups or charged carboxylate groups (—$COO^-$). The oxidized cellulose employed in the present invention may be synthetic, semi-synthetic or commercially attained. The oxidized cellulose may also be in its crystalline form, amorphous form or may be partially crystalline and partially amorphous.

In one embodiment, the oxidized cellulose is amorphous oxidized cellulose.

In another embodiment, the oxidized cellulose is in the form of microparticles.

In another embodiment, the oxidized cellulose is in the form of nanoparticles.

Oxidation of cellulose may be achieved by various synthetic pathways as may be known to the artisan (see for example Kumar et al, 2002). Such oxidation, preferably does not substantially affect the glucose ring structure, although a certain degree of ring opening may occur depending on the oxidative conditions employed. The degree of oxidation of the hydroxymethylene groups may be quantified (for example by titration) and the percent weight of the —COOH groups from the total weight of the polymer (or percent oxidation) may be calculated. On average, the percent weight of —COOH was 20% of the total weight of the oxidized cellulose.

In one embodiment, the % percent weight of the —COOH groups is at least 3% of the total weight of the oxidized cellulose.

In another embodiment, the % weight of the —COOH groups of the total weight of the oxidized cellulose is between 3 and 25%.

The microparticles and/or nanoparticles of oxidized cellulose may be prepared by any method known suitable for the reduction of particle size. Preferably, the microparticles and/or nanoparticles of oxidized cellulose are prepared by milling the already oxidized cellulose to a desired particle size, typically in the range of about 0.01 and 100 microns. Smaller and larger particles have been obtained. The determination of particles size as well as of shape may be achieved, as disclosed hereinbelow, by any measuring technique known to an artisan, such as light and electron microscopies, X-ray diffraction, etc.

Thus the present invention further provides a method for the preparation of microparticles and/or nanoparticles of oxidized cellulose said method comprising obtaining oxidized cellulose and affecting a reduction in particle size to the desired size.

In one embodiment, the oxidized cellulose is in the form of solid particulates.

In another embodiment, the reduction in particle size immediately follows the production of the oxidized cellulose.

In another embodiment, the oxidized cellulose is commercially obtained.

In another embodiment, the reduction in particle size is achieved by milling.

In yet another embodiment, the reduction in particle size affords a mixture of microparticles and nanoparticles of oxidized cellulose.

In still another embodiment, the reduction in particle size affords microparticles.

In still another embodiment, the reduction in particle size affords nanoparticles.

In still another embodiment, the manufactured microparticles or nanoparticles are further chemically transformed to a salt or a derivative of said oxidized cellulose.

The oxidized cellulose may be used in the composition of the invention in one or more of the following forms:

(a) acidic form, having substantially all carboxylic groups protonated, namely in the form of —COOH, (b) salt form, having some or all of the oxidized groups in the charged carboxylate form, namely in the form of —COOX, wherein X is a monovalent, divalent or multivalent metal ion selected for example amongst alkali and alkaline metal ions, (c) derivatized form, having some or all of the oxidized groups in the form —COOR, wherein R is an organic radical selected amongst substituted or unsubstituted C1-C20 alkyl, cycloalkyl, alkylene or cycloalkylene; substituted or unsubstituted C6-C12 aryl or arylene; substituted or unsubstituted C5-C12 heteroaryl or heteroarylene (having at least one heteroatom selected from N, O, S), C2-C20 alkenyl, alkenylene, cycloalkenyl or cycloakenylene; wherein each of said groups may be substituted by one or more organic or inorganic atom or (groups such as halogens (Br, Cl, I, F), nitro, amines (primary, secondary or tertiary), alkyls, aryls and others as may be known to a person skilled in the art. The chemical transformation to the derivatized form, from the acid or salt forms, may be achieved by any transformation known to the person skilled in the art. In this respect, see for example "Comprehensive Organic Functional Group Transformations, Second Ed., by Alan R. Katritzky and Richard J. K. Taylor, 2004.

The bond between the O atom of the carboxylic moiety of the oxidized cellulose and the atom of the R group may be an ionic bond (such as in the case of a salt of metal or non-metal ions such as ammoniums) a covalent bond, a coordination bond or any other interaction which is capable of holding the two moieties—the oxidized cellulose and the R moiety—in close proximity. In one embodiment, the bond is a covalent bond. In another embodiment, the covalent bond is a hydrolysable bond.

In some embodiment, the oxidized cellulose is a derivatized oxidized cellulose having at least 0.05% of its oxidized groups bonded (ironically, covalently, via coordination, etc.) to at least one R moiety being at least one pharmaceutical (drug). Such drugs may be selected from anti-asthma drugs, anti-allergy drugs, antihistamine drugs, smooth muscle cell relaxing agents (e.g., linalool, magnesium sulfate), mast-cell stabilizers, anti-IgE drugs, analgesics, hormones, steroids, anti-inflammatory drugs, antibiotics, anti-viral drugs, anti-bacterial drugs, anti-fungal drugs, selective or non-selective potassium channel activators (bronchodilatators), muscarinic M3 receptor antagonists, M2 receptor agonists, opioid receptor agonists, H3-receptor agonists (inhibit acetylcholine release), phospholipase A2 inhibitors, 5-lipoxygenase inhibitors, 5-lipoxygenase activating protein (FLAP) inhibitors, leukotriens modifier drugs, leukotriens receptor antagonists, phosphodiesterase inhibitors, immunomodulating agents (e.g., ciclosporine), antibodies against adhesion molecules, antagonists of tachykinins, mucus secretion inhibitors, inhaled DNAs (Dronase) and other mucus liquefying agents, anti-oxidative agents and oxygen radical scavengers.

Non-limiting examples of such drugs are dexamethasone, triamcinolone acetonide, beclomethasone, dipropionate, flunisolide, fluticasone propionate, prednisone, methylprednisolone, mometasone furoate, chlorcyclizine, chlorpheniramine, triprolidine, diphenhydramine hydrochloride, fexofenadine hydrochloride, hydroxyzine hydrochloride, loratadine, promethazine hydrochloride, pyrilamine, omalizumab, albuterol, pirbuterol, epinephrine, racepinephrine, adrenaline, isoproterenol, salmeterol, metaproterenol, bitolterol, fenoterol, formoterol, isoetharine, procaterol, penicillin G, ampicillin, methicillin, oxacillin, amoxicillin, cefadroxil, ceforanid, cefotaxime, ceftriaxone, doxycycline, chlortetracycline, minocycline, tetracycline, amikacin, gentamycin, kanamycin, neomycin, streptomycin, netilmicin, paromonmycin, tobramycin, azithromycin, clarithromycin, erythromycin, ciprofloxacin, lomefloxacin, norfloxacin, chloramphenicol, clindamycin, cycloserine, isoniazid, rifampin, vancomycin, aztreonam, clavulanic acid, imipenem, polymyxin, bacitracin, amphotericin, nystatin, nevirapine, delavirdine, efavirenz, saquinavir, ritonavir, indinavir, nelfinavir, amprenavir, zidovudine, stavudine, larnivudine, didanosine, zalcitabine, abacavir, acyclovir, penciclovir, valacyclovir, ganciclovir, 1-D-ribofuranosyl-1,2,4-triazole-3 carboxamide, 9,2-hydroxy-ethoxy methylguanine, adamantanamine, 5-iodo-2'-deoxyuridine, trifluorothymidine, interferon, adenine arabinoside, benzoic acid, undecylenic alkanolamide, ciclopiroxolamine, polyenes, imidazoles, allylamine, thicarbamates, amphotericin B, butylparaben, clindamycin, econaxole, amrolfine, butenafine, naftifine, terbinafine, ketoconazole, elubiol, econazole, econaxole, itraconazole, isoconazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, fluconazole, flutrimazole nystatin, pimaricin, flucytosine, natamycin, tolnaftate, mafenide dapsone, caspofungin, actofunicone, griseofulvin, potassium iodide. Gentian Violet, ciclopirox, ciclopirox olamine, haloprogin, ketoconazole, linalool, undecylenate, silver sulfadiazine, undecylenic acid, undecylenic alkanolamide and Carbol-Fuchsin.

Other drugs may be cytokines and chemokines, particularly anti-inflammatory cytokines such as IL-4 and IL-10.

The drugs may be bonded to the oxidized cellulose as discussed above (i.e., ionically or covalently through the carboxylic group) or through any other atom on the glucose monomers (e.g., the hydroxy moieties) via any atom of the drug molecule. In some embodiments, the drug molecule possesses an atom that may be used for bonding to the oxidized cellulose (For example a heteroatom via which binding to the oxidized cellulose may take place or a pendent group which may directly interact with an atom or group of the oxidized cellulose). In some other embodiments, the binding of the drug to the oxidized cellulose necessitates a chemical group transformation as may be known to a person skilled in the art.

In some other embodiments, the drug is associated with the oxidized cellulose via a non-covalent bonding.

The compositions of the invention may comprise any combination of glucans, or oxidized celluloses. In one embodiment, the composition comprises a single form of the oxidized cellulose, e.g., only amorphous oxidized cellulose, preferably in the form of micro or nanoparticles. In another embodiment, the composition comprises at least two forms of oxidized cellulose, for example nanoparticles in combination with microparticles. In another embodiment, the composition comprises oxidized cellulose and an oxidized cellulose derivative.

In some embodiments, the at least one glucan, e.g., oxidized cellulose may be part of a core-shell system, a lipid vesicle, a liposome, or any other carrier having an inner core containing the oxidized cellulose and optionally at least one additional additive or solvent, and a shell which substantially surrounds it. Alternatively, the core may contain optionally an additive or a solvent and the shell which substantially surrounds it may be the glucan, a salt or derivative thereof.

The pharmaceutical composition of the present invention may further comprise at least one drug or therapeutics as detailed hereinbefore and any other additive as disclosed hereinbelow.

The compositions of the present invention may be adapted and/or packaged as a kit for personal use or for use by a medical practitioner, for periodic administration to a subject in doses over any period of time.

Typically, for the prevention or treatment of allergies and related diseases or disorders, the period is of 3-30 days, in doses at least once daily up to ten times/day. The composition may for example contain in each one of said doses up to 2 g of the glucan, e.g., oxidized cellulose, salt or a derivative thereof. In another example, dosages of about 200-1,000 mg of the glucan, adapted for administration to said subject may be prepared in capsules, tablets, lozenges, as a powder, a suspension, syrup, a cream, eye or nasal drops or ointment, etc.

As used herein, the term "subject" includes animals, particularly mammalian animals, and most preferably humans. Non-human animals include for example primates, domestic animals, farm animals, and experimental animals. The term also encompasses all animal disease models for e.g., asthma and allergy and naturally occurring or non-naturally occurring mutated or non-human genetically engineered (e.g., transgenic or knockout) animals.

As stated hereinbefore, the compositions of the invention are used for the treatment and/or prophylaxis of at least one disease or disorder associated with at least one allergen. The term "allergen" refers to all foreign agents capable of inducing, promoting, or stimulating allergy, i.e., the hypersensitive state induced by an exaggerated immune response to the allergen, or asthmatic reaction in a subject. The term encompasses plant/tree pollens or spores, animal dander, house dust mite, dust, lint, mite feces, fungal spores, and cockroaches. In one preferred embodiment, said allergen is pollen.

Non-limiting examples of plant or tree pollen include:
weed pollen such as, but not limiting to, dandelion, goldenrod, nettle, sage, clover, ragweed, mugwort, pellitory, nettles and dock;
grass pollen such as, but not limiting to, Bermuda couch grass, sweet vernal grass, red and blue grasses, Johnson grass pollen; ryegrass such as Italian or annual ryegrass, perennial ryegrass, hybrid ryegrass, timothy grass, orchard grass, tall fescue, meadow fescue and red fescue;
tree pollen such as, but not limiting to, alder, oak, ash, cypress, olive, maple, cedar, western red cedar, elm, birch, hickory, poplar, American sycamore, and walnut; and
annual plant pollen such as, but not limiting to, tobacco and cotton.

Animal allergens may for example be skin, hair, various parasites and fungi. In one particular embodiment, the animal allergen is associated with cat allergens.

As may be known to the person skilled in the art, when the allergen enters the respiratory system or when coming in contact with the skin or eyes it induces an array of diseases or disorders which may be directly caused by the allergen, and thus is referred to as a "disease or disorder mediated by" the allergen. Alternatively, the disease or disorder, although initially not mediated by the allergen, may deteriorate due to exposure to an allergen. Limiting or avoiding contact of a tissue with said allergen may prevent or lessen such disease or disorder. Such a disease or disorder which deteriorates by allergen contact is referred to as a disease or disorder which is "associated with at least one allergen.". In its broadest definition, this expression is used to mean that there exists a relationship between an exposure to an allergen and the induction of a symptom, a condition, a disorder or a disease, or that there exists a secondary effect of the exposure to the allergen which exacerbates a condition, a disorder or a disease that may have been initially caused by another factor. One association may for example be between a disease which is either caused by binding of IgE to an allergen causing immediate Type I allergic reaction or to a disease that is caused by another factor aggravated by the IgE-allergen interaction. A symptom that is present in a subject may therefore be the direct result of or caused by the exposure to the allergen.

Examples of such a disease or a disorder are the inflammatory, allergic and non-allergic diseases or disorders of the respiratory system or the skin. An inflammatory condition, disorder or disease refers to one or more physiological responses that characterize or constitute inflammation. An allergy or allergic condition, as used herein refers to a hypersensitivity to an allergen. Such conditions, disorders and diseases include but are not limited to allergic asthma, asthma, extrinsic bronchial asthma, chronic obstructive pulmonary disease, hay fever (seasonal rhinitis), allergic rhinitis, allergic conjunctivitis, hives, eczema, urticaria, angioedema, onchocercal dermatitis, atopic dermatitis, dermatitis, swelling, hypersensitivity pneumonitis and bronchopulmonary dysplasia.

In one embodiment, the disease or disorder associated with at least one allergen is allergic rhinitis, allergic conjunctivitis, hives, hay fever and asthma of any type and in particular seasonal asthma, allergic skin diseases including urticaria, angioedema and atopic dermatitis. In another embodiment, the disease or disorder is asthma or allergic rhinitis.

Asthma refers herein to an allergic or non-allergic condition, disorder or disease of the respiratory system that is episodic and characterized by inflammation with constriction, narrowing or obstruction of the airways. Allergic asthma is typically associated with increased reactivity of respiratory system to an inhaled allergen. Asthma is frequently, although not exclusively associated with atopic or allergic symptoms. Typically, a subject with asthma suffers from recurrent attacks of cough, shortness of breath with wheezing, chest pain, chest tightness, etc. While a plurality of such adverse symptoms typically occur in asthma, the existence of any one is usually adequate for diagnosis of asthma, and for treatment in accordance with the invention. Asthmatic conditions can be acute, chronic, mild, moderate or severe asthma (unstable asthma), nocturnal asthma or asthma associated with psychological stress.

Allergic rhinitis is an allergic reaction of the nasal mucosa (upper airways), which includes hay fever (seasonal allergic rhinitis) and perennial rhinitis (non-seasonal allergic rhinitis) which are typically characterized by seasonal or perennial sneezing, rhinorrhea, nasal congestion, pruritis and eye itching, redness and tearing.

The composition may also comprise a pharmaceutically acceptable carrier, such as a vehicle, an adjuvant, an excipient, or a diluent. Such carriers are well known to those who are skilled in the art and are readily available to the public. It is preferred that the pharmaceutically acceptable carrier be one which is chemically inert to the glucan or oxidized cellulose or any other component of the composition and one which has no detrimental side effects or toxicity under the conditions of use.

The choice of carrier will be determined in part by the particular composition, as well as by the particular method used to administer the composition. Accordingly, there is a wide variety of suitable formulations of the pharmaceutical composition of the present invention. The following formulations for topical, oral, aerosol, intranasal, intraocular, parenteral, subcutaneous, intravenous, intramuscular, interperitoneal, rectal, and vaginal administrations are merely exemplary and are in no way limiting.

Formulations for topical application on the skin of the subject or on the subject's hair may be in the form of a gel, ointment, emulsion, thick cream, liniment, balsam, lotion, foam, mask, shampoo, tonic means, cleaner, spray, hair spray, (or it may be in the form of a means for the hair treatment such as rinsing, coloring, discoloring, hairdressing, hair straitening, hair waving, or hair fixing), powder including liquid powder, compact powder, cosmetic pencil, or in any other traditional form used in the field of cosmetology or dermatology.

Formulations suitable for oral administration can consist of (a) liquid solutions, such as an effective amount of the oxidized cellulose dissolved in diluents, such as water, saline, or orange juice; (b) capsules, sachets, tablets, lozenges, and troches, each containing a predetermined amount of the oxidized cellulose, as solids or granules; (c) powders; (d) suspensions in an appropriate liquid; and (e) suitable emulsions. Liquid formulations may include diluents, such as water and alcohols, for example ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and starch. Tablet forms can include one or more of lactose, sucrose, mannitol, corn starch, potato starch, alginic acid, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the oxidized cellulose in a flavor, usually sucrose and acacia or tragacanth, as well as pastilles comprising the active ingredient in an inert base, such as gelatin and glycerin, or sucrose and acacia, emulsions, gels, and the like containing, in addition to the oxidized cellulose, such carriers as are known in the art.

The compounds of the present invention, alone or in combination with other suitable components, can be made into aerosol formulations to be administered via inhalation or intranasally. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations for intranasal or mucosal delivery may comprise enhancing agents such as solubilization agents; charge modifying agents; pH control agents; degradative enzyme inhibitors; mucolytic or mucus clearing agents; ciliostatic agents; membrane penetration-enhancing agents such as surfactants, bile salts, phospholipid or fatty acid additives, mixed micelle, liposome, or carrier, alcohols, enamines, NO donor compounds, long-chain amphipathic molecules, small hydrophobic penetration enhancers; sodium or a salicylic acid derivatives, glycerol ester of acetoacetic acids, cyclodextrin or beta-cyclodextrin derivatives medium-chain tatty acids, chelating agents, amino acids or salts thereof, N-acetylamino acids or salts thereof, enzyme degradatives to a selected membrane component, inhibitors of fatty acid synthesis, inhibitors of cholesterol synthesis; or any combination of these membrane penetration enhancing agents; modulatory agents of epithelial junction physiology, such as nitric oxide (NO) stimulators, chitosan, and chitosan derivatives; vasodilator agents; selective transport-enhancing agents; and stabilizing delivery vehicles, carriers, supports or complex-forming species which is/are effectively combined, associated, contained, encapsulated or bound to stabilize the oxidized cellulose for enhanced mucosal delivery.

In some embodiments of the invention, the mucosal therapeutic and prophylactic compositions of the present invention may be supplemented with any suitable penetration-promoting agent that facilitates absorption, diffusion, or penetration of the composition or any component thereof across mucosal barriers.

Certain formulations for intranasal applications as for aerosol applications are specifically adapted for a selected target cell, tissue or organ, which are at a remote target site or even a particular disease state. Efficiently loaded formulations at effective concentration levels in a carrier or other delivery vehicle, may be delivered and maintained in a stabilized form, e.g., at the nasal mucosa and/or during passage through intracellular compartments and membranes, to a remote target site for action (e.g., a defined tissue, organ, or extracellular compartment).

Formulations for intraocular administration may be administered topically to the eye or eye lid, for example, using drops, an ointment, a cream, a gel, a suspension, etc. The oxidized cellulose may be formulated with excipients such as methylcellulose, hydroxypropyl methylcellulose, hydroxypropyl cellulose, polyvinyl pyrrolidine, neutral poly (meth) acrylate esters, and other viscosity-enhancing agents.

Formulations suitable for parenteral administration include aqueous and non-aqueous, isotonic sterile injection solutions vehicle can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The oxidized cellulose can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts and (3) mixtures thereof.

The parenteral formulations will typically contain from about 0.05 to about 25% by weight of the oxidized cellulose in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose scaled containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compositions of the present invention may be made into injectable no formulations. The requirements for effective pharmaceutical carriers for injectable compositions are well known to those of ordinary skill in the art. See for example *Pharmaceutics and Pharmacy Practice*, J.B. Lippincott Co., Philadelphia, Pa., Banker and Chalmers, eds., pages 238-250 (1982), and *ASHP Handbook on the Injectable Drugs*, Toissel, 4th ed., pages 622-630 (1986).

Additionally, the compositions of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In one embodiment of the invention, the composition is a topical composition formulated for administration onto the skin (including eyes, scull), hair and nails) of a subject.

In another embodiment, the composition is formulated for mucosal application.

In another embodiment, the composition is Formulated for oral administration.

In another embodiment, the composition is formulated for intraocular administration e.g., as eye drops, crème, etc.

In another embodiment, the composition is formulated for intranasal administration.

In another embodiment, the composition is formulated for inhalation.

Subjects predisposed or susceptible to, exposed to or allergic to allergens such as those disclosed herein may be at risk of having asthma and, therefore, are amenable to treatment in accordance with the invention. The compositions of the invention are also useful for contacting with or administering to subjects prophylactically, namely prior to manifestation or onset of asthma or any other condition or an associated symptom or physiological or psychological response, such that it can eliminate, prevent, inhibit, decrease or reduce the probability, susceptibility or frequency of having asthma or an associated symptom.

In another aspect of the present invention, there is provided a method for the treatment or prophylaxis of at least one disease or disorder mediated by or associated with at least one allergen, said method comprising administering to a subject an effective amount of at least one glucan. In one embodiment, said at least one glucan is oxidized cellulose, a salt or derivative thereof.

As stated hereinbefore, the glucan is not cellulose or any non-oxidized form thereof.

In one embodiment of the present invention, said subject is one suffering from said disease or disorder.

In another embodiment, said subject has a predisposition to said disease or disorder. The predisposition may be genetic or environmental.

In another embodiment, said at least one disease or disorder is an allergic reaction.

In another aspect of the present invention, there is provided method for delaying the onset or lessening the severity of at least one allergic reaction, said method comprising administering to a subject an effective amount of at least one glucan. In one embodiment, said at least one glucan is oxidized cellulose, a salt or derivative thereof.

The invention further provides a method for reducing a subject's sensitivity to at least one allergen, said method comprising administering to said subject an effective amount of at least one glucan. In one embodiment, said at least one glucan is oxidized cellulose, a salt or derivative thereof.

The invention further provides a method of reducing a subject's sensitivity to a pollen allergen in a subject sensitive to such pollen allergen or a second allergen immunologically cross-reactive with said pollen allergen, comprising administering to said subject at least one glucan. In one embodiment, said at least one glucan is oxidized cellulose, or a salt or derivative thereof.

The methods and compositions of the present invention are appropriate for treatment of subjects exposed to an allergen or who are susceptible to having an allergic reaction. Within the scope of the present invention, subjects who are at risk of having an allergic reaction include subjects having a predisposition towards an allergic reaction, or infection or exposure to an agent that is associated with an allergy or allergic reaction due to a genetic or environmental risk factor. Subjects having a predisposition can be identified by a personal or family history, through genetic screening, tests appropriate for detection of increased risk, or exhibiting relevant symptoms indicating predisposition or susceptibility. The allergic reaction may be any such symptom or condition associated with, for example, an existing allergic condition, a symptom or condition associated with or caused by an allergic condition, an acute allergic episode, a latent allergic condition, and seasonal or geographical tendencies.

The methods of the invention are directed at providing a beneficial effect or therapeutic benefit to a subject, either short-term and/or longer-term. Thus, the term "treatment" or any lingual variation thereof, refers within the scope of the present invention to a clinical endpoint characterized by an improvement in the subjects condition; a reduction in the severity, frequency, duration or progression of one or more adverse symptoms or complications associated with the disease or disorder; and/or an inhibition, reduction, elimination, prevention or reversal of one or more of the physiological, biochemical or cellular manifestations or characteristics of the disorder or disease, including complete prevention of the disease or disorder.

Thus, in one embodiment of the methods of the invention, the treatment and/or prophylaxis of at least one disease or disorder associated with at least one allergen comprises reducing progression, severity, frequency, duration, susceptibility or probability of inflammatory, allergic and non-allergic conditions, disorders and diseases of a subject suffering from any one of such conditions or having a genetic or environmental predisposition to having one or more of the conditions, symptoms, diseases or disorders.

In one embodiment, the disease or disorder is asthma and the condition or symptom is any one symptom associated with asthma.

In order to achieve any one of the therapeutic benefits of the compositions and methods of the invention, the active component, namely the at least one glucan, being preferably an oxidized cellulose, a salt or a derivative thereof, should be administered therapeutically or prophylactically in an efficient amount which may vary according to the status of the condition, the type of treatment sought (i.e., therapeutic or preventive), the general condition of the subject, the use of other drug or agent and any other factor as may be known to a medical practitioner. The dose amount, frequency or duration of administration may be proportionally increased or reduced. The term "effective amount" or any lingual variation thereof, refers generally to a therapeutic or prophylactic amount which is, when administered to a subject, sufficient to reduce, prevents delay and/or inhibit the onset or progression or worsening of a disease or disorder; to reduce relieve, and/or alleviate the severity, frequency, duration, susceptibility or probability of one or more undesirable symptom or condition associated with the disease or disorder; to hasten the recovery from one or more symptoms associated with the disease or disorder.

The treatment or prophylactic regimens may be short term or long term and may depend on such factors as discussed hereinabove. The compositions or methods of the invention may employ a single administration of any one composition or multiple administrations, wherein the composition is administered alone or in combination with other therapeutics or treatments.

Without wishing to be bound to specific dosages and particular regimes, as the therapeutic or prophylactic efficacy of the compositions and methods of the invention may vary between one subject to another, a subject may be administered a composition of the invention once, twice, three, four, five or more times daily, weekly, monthly or annually. Depending on the therapeutic effect sought, therapeutic or a prophylactic, and the type of formulation, e.g., for oral, nasal or topical administration, the dose size may vary between about 0.1 mg/kg, to about 100 mg/kg.

The composition of the invention may be administered by a medical practitioner or by the subject being treated prior to an expected contact with an allergen, immediately after such a contact, or within a short period after the onset of at least one symptom associated with a disease or disorder.

Apart from the manufacture of the pharmaceutical compositions of the invention, according to another aspect of the present invention, the at least one glucan, and most preferably the oxidized cellulose, a salt or derivative thereof is also used for the preparation of compositions or formulations for non-therapeutic purposes having to do with the reduction or complete elimination of a plurality of allergen from an environment.

According to this aspect of the invention the at least one glucan, preferably the oxidized cellulose, a salt or derivative thereof, may be employed as an allergen inactivator in the manufacture of such paper products such as a mask, a sheet; air filtering units; cosmetic products such as a crème, a spray, an aerosol; household solutions such as a detergent, a laundering agent; etc. The at least one glucan may be embedded in the material from which the object is prepared or may be applied thereon by distributing, spraying, coating, or evaporating a solution or formulation containing thereof. The allergen inactivating formulation may be applied to any surface suspected of having to thereon allergens.

BRIEF DESCRIPTION OF THE DRAWINGS in order to understand the invention and to see how it may be carried out in practice, embodiments will now be described, by way of non-limiting example only, with reference to the accompanying drawings, in which:

FIGS. 1A-1D demonstrates the efficacy of the compositions of the present invention in animal model. BALB/c mice (3 groups) were sensitized intranasally with 100 µg/animal of grass pollen soluble proteins in 50 µl PBS on days 0, 1, and 2 and challenged on days 14, 15, 18, and 19 intranasally with 25 µg grass pollen soluble proteins. A naïve control was made by intranasally treating BALB/c mice with PBS. On day 21 mice one group of asthmatic mice and the naïve mice were sacrificed and BALF were obtained. Total BALF cells were counted (FIG. 1A) and cells were stained by May-Grunwald Giemsa and were characterized morphologically (FIG. 1B). On day 26 the remaining two asthmatic groups received a challenge by inhalation of either pollen proteins only or pollen proteins with OCAM. Mice were sacrificed at day 29 and BALF were obtained. Total BALF cells were counted (FIG. 1C) and cells were stained by May-Grunwald Gieemsa and were characterized morphologically (FIG. 1D).

FIGS. 2A and 2B demonstrate the specific binding of microcrystalline non-oxidized cellulose to major rye grass allergens. Soluble pollen proteins were bound to either KOH-washed or untreated non-oxidized cellulose particles. Both bound (labeled B) and unbound (labeled UB) fractions (20 μL), were separated on a 4-20% glycine gradient gel or 150% glycine gel. Gels were stained with either coomasie stain (FIG. 2A) or Silver stain (FIG. 2B).

FIGS. 3A and 3B demonstrate that oxidation of microcrystalline cellulose into oxidized cellulose increases dramatically its ability to bind rye grass pollen allergens. Soluble pollen proteins from either *Lolium perenne* (FIG. 3A) or *Lolium rigidum* (FIG. 3B) were bound to either oxidized cellulose (prepared from Avicel microcrystalline cellulose) or to non-oxidized Avicel microcrystalline cellulose. Bound (labeled B) and unbound (labeled UB) fractions and total proteins (labeled T) were separated by SDS-PAGE and stained by coomassie.

FIG. 4 demonstrates the binding of beta-glucan to rye-grass pollen proteins. Soluble pollen proteins were bound to different quantities of beta-glucan. Both bound (labeled B) and unbound (labeled UB) fractions were separated by 15% glycine gel and stained with silver stain.

DETAILED DESCRIPTION OF EMBODIMENTS

Figure 5A:
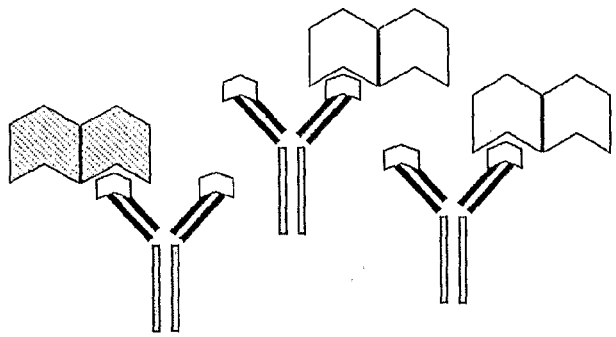
FIGS. 5A-5C illustrate the general concept of a oxidized-cellulose blocking mechanism.
Figure 5B:
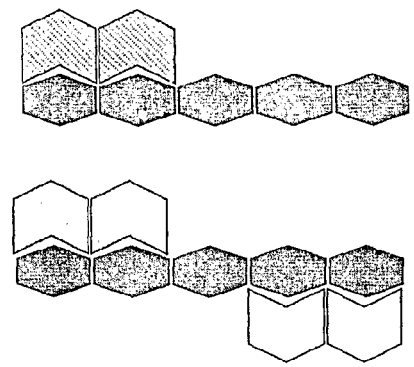
Figure 5C:
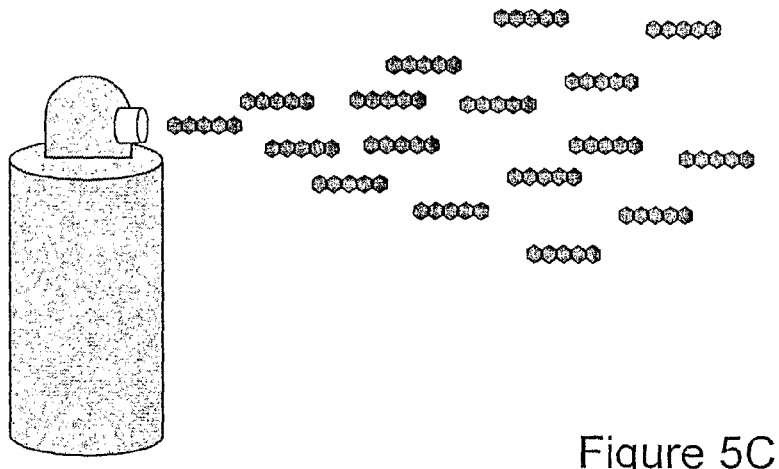

As disclosed herein, glucans and particularly oxidized cellulose have the necessary recognition of various plants allergens and the capability of binding thereto. Without wishing to be bound by theory and as illustrated for the sake of general understanding of the invention in FIGS. 5A, 5B and 5C, pollen allergens from groups I, II, or III bound by specific IgE antibodies of allergic patients can induce an allergic reaction (FIG. 5A). Pollen allergens can also bind glucans and polysaccharides such as oxidized cellulose through there CBD, cellulose binding domain (FIG. 5B). Since most of the IgE binding domains of pollen allergens of groups I, II and III are found in their CBD, polysaccharides such as oxidized cellulose can compete with IgE specific antibodies on allergen binding and thereby inhibit the allergic reaction. The employment of pharmaceutical compositions comprising such glucans by patients by various application methods such as by spraying the composition onto the skin or tissue (FIG. 5C), assists in the formation of a reactive barrier that prevents the association of the allergen and the antibodies.

Figure 6A:
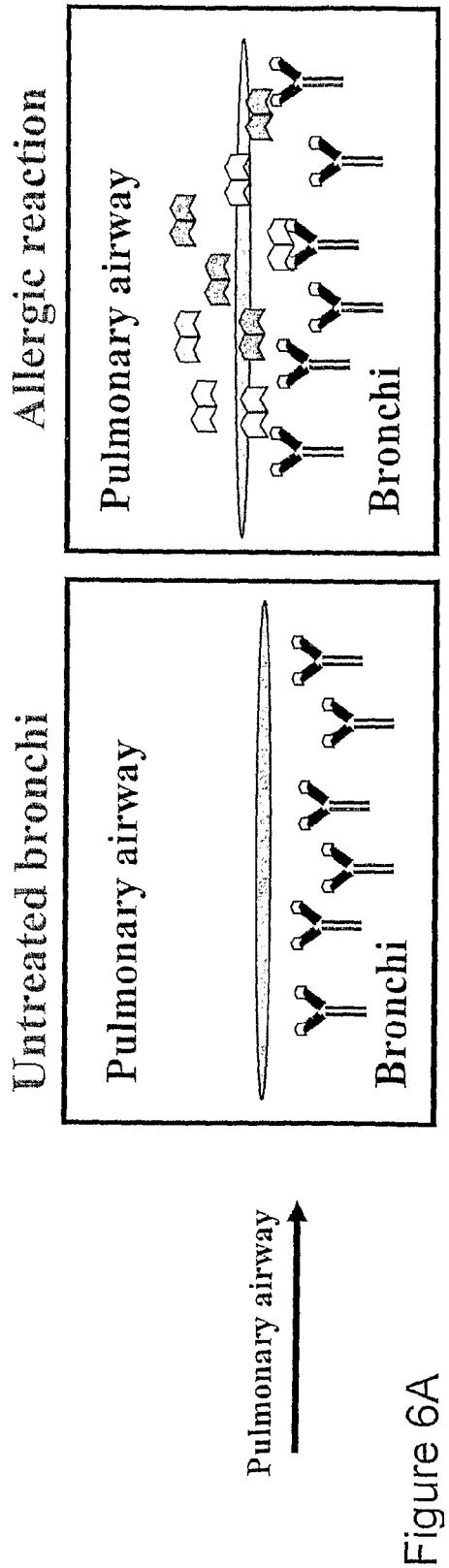
FIGS. 6A and 6B illustrate an exemplary application of a composition of the invention by inhalation.
Figure 6B:
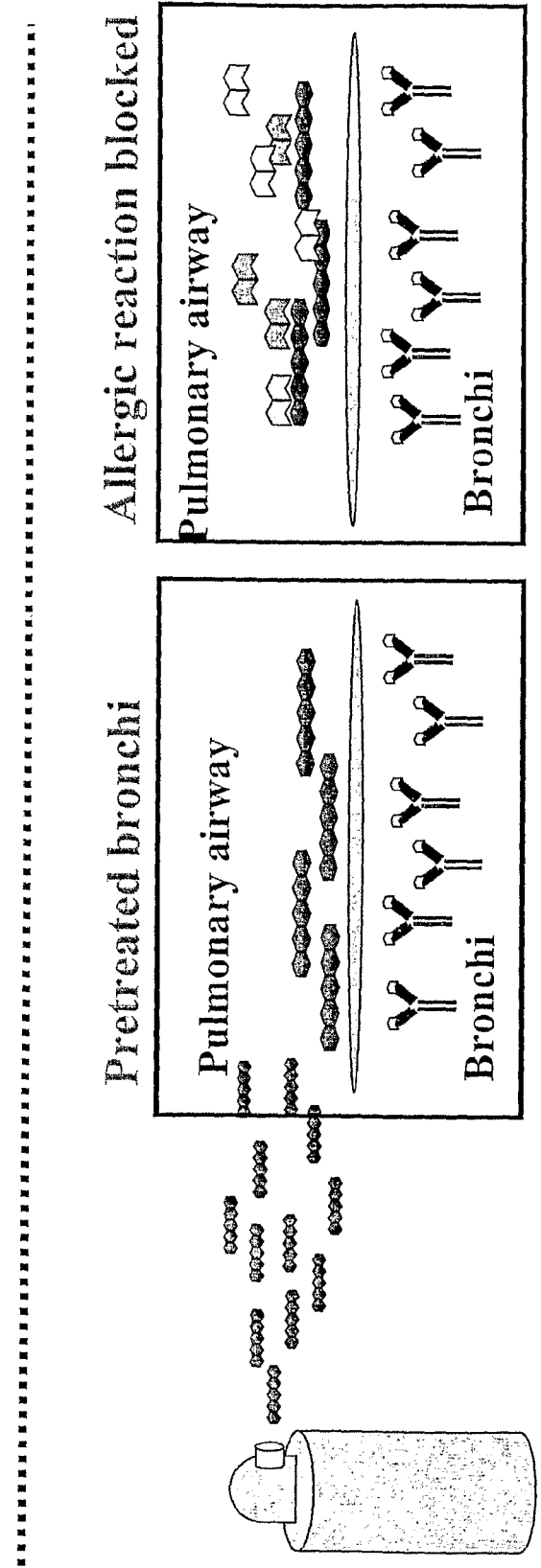

As FIGS. 6A and 6B further illustrate, allergen specific IgE antibodies may encounter pollen allergens of group I, II, or III in the bronchi of allergic patients and thus induce an allergic reaction (FIG. 6A). The application of glucans such as to oxidized cellulose to the patient's bronchi prevents the binding of pollen allergen to IgE specific antibodies and thereby inhibits the allergic reaction (FIG. 6B). It has been demonstrated that the glucans can prevent allergen binding to IgE either through direct competition or by creation of a relatively large allergen-glucan complex that is removed from the bronchi, through mucociliary transport.

While FIGS. 5A-5C and 6A-6B illustrate specifically oxidized cellulose and application thereof by inhalation, it should be understood that this example is provided as a single illustration and should not be taken to be any limitation of scope. The compositions of the invention may be applied to a target organ or tissue by ally method known and in any dosage as may be necessitated by the condition, the severity thereof, the subject, and other parameters as known to a medical practitioner.

EXAMPLES

Example 1

Preparation of Various Oxidized Cellulose Amorphous Microparticles (OCAMs)

Different Oxidized Cellulose Amorphous Microparticles (OCAMs) with different degree of crystallinity and oxidation were prepared essentially as described by Kumar et al (2002).

Briefly, nitric acid and phosphoric acid were mixed in 4:1 (v/v) ratios. To a 140 ml solution of the acid mixture, 10.0 g of microcrystalline cellulose was added. Once the cellulose was completely soaked. 2.0 g of sodium nitrite were added in one portion. An immediate formation of reddish brown fumes occurred. The reaction mixture was allowed to react at room temperature. With occasional stirring, for 24 hours. The reaction mixture, which appeared green in color, was terminated by adding 700 ml of doubly distilled water (DDW). The diluted reaction mixture was filtered, and the white fluffy solid obtained was washed with water until the filtrate showed a pH of about 4. The solid was washed with acetone and then air-dried at 60° C. and at room temperature. The dried oxidized cellulose was milled to 10 microns by a vortexmill (Super Fine, Israel). The distribution of the particles size was determined by MASTERSIZER 2000 MALVERN (England) and was from 1-10 microns.

The particle size can be changed by milling to different sizes using, any one milling apparatus. Size and shape were determined by light and electron microscopy. Degree of crystallinity was determined by X-ray diffraction.

In some embodiments of the invention, the thus prepared OCAMs may be reacted with various glucans by mixing the OCAMs with a solution of the glucan. The glucan may be one or more selected amongst rye flour arabinoxylan, barely beta-glucan, oat beta-glucan Galacton® (Lupin), pullulan, carob galactomannan, xyloglucan, guar galactomannan, pectic galactan, rhamnogalacturonan-galacturonic acid, pachyman, curdlan, and mannan. The glucans adsorb to the cellulose by non-covalent bonding. After binding, the unbound material is removed and the particles are dried to remove the remaining solvent.

In other embodiments, the particles are of chitosan and not oxidized cellulose.

Example 2

Determination of Optimal Allergen Blocking OCAMs

Different preparations of OCAMs are used in-vitro to block different allergen preparations and prevent IgE binding of sera from allergic patients. Aqueous solutions containing different pollen protein allergens are incubated with different OCAMs. The particles are removed by centrifugation and the resulted proteins are tested for IgE binding using ELISA. OCAMs that show the highest IgE blocking activity are used for further analysis. Histamine release is performed with heparinized whole blood as described by Shirai et al., (1997). The patients, men and women with pollen-induced asthma, who had been diagnosed by skin test and inhalation challenge are treated. As controls are chosen asthmatic subjects with no response to pollen allergen.

Heparinized whole blood samples are taken and incubated with pollen allergens in the presence or absence of selected OCAMs at various concentrations for 30 minutes at 37° C. After centrifugation, histamine levels are measured in the cell-free supernatants by histamine ELISA kit (IBL, Hamburg Germany). Histamine release is expressed as a percentage of total histamine. Successful OCAMs are chosen based on their ability to block wide spectrum of allergens and reduce or even prevent histamine release.

Example 3

Determination of Allergy Blocking by OCAM in an Animal Model

The following is a basic protocol developed for determining the efficacy of the compositions and methods of the invention on animals. A person skilled in the art would appreciate that this protocol may be regarded of only one example and that other more specific or more generic models may be developed for the purpose.

In the following, female, 8-9 week old BALB/c mice are used for asthma model. Mice are divided into 3 treatment groups (naïve, asthma, and treatment groups) 10 mice in each group. Naïve mice are used as negative controls and are challenged with normal saline instead of the grass pollen allergen. 20 mice are sensitized as described below. 10 mice are treated with OCAM inhalation before each allergen challenge (treatment group).

Grass pollen is used for the preparation of an extract. Five grams of pollen are suspended in 50 ml phosphate buffered saline (PBS) and extracted by stirring at room temperature for 15 minutes. After centrifugation at 20000×g for 10 min at 4° C. the supernatant is filtered through a 0.45-micron filter. The protein concentration of the grass pollen extract is determined using the BCA reagent (Pierce).

For sensitization 100 µg/animal grass pollen adsorbed to Al(OH)$_3$ (2 mg/animal) is injected intraperitoneally (i.p.) three times in 14-day intervals. Animals are challenged by either allergen inhalation (1 mg/ml) for 10 minutes each time with the mice placed unrestrained in a 20-liter box connected to an ultrasonic nebulizer (LS 230 System Villeneuve Sur Lot, France) or intranasal administration (25 µg/animal) in 50 µl PBS on day 0, 3 and 6 after the last injection. Alternatively, mice can be challenged once or twice at days 20-24.

Bronchoconstriction is measured at any of the days of the challenge or in the days that follow the 6 day challenge by a modified noninvasive method (Hamelmann et al. 1997) using barometric plethysmography and expressed as the enhanced pause (Penh), a calculated dimensionless value that correlates with measurement of airway resistance, impedance, and intra-pleural pressure. Penh is measured before (as baseline) and after each allergen challenge. Data is expressed as the percent change of Penh compared to baseline (% Penh).

Mice are sacrificed under deep anesthesia with 2,2,2 tribromoethanol solution 24-72 hours after the last challenge. A midline celiotomy is performed, and the animals are euthanized by exsanguination by withdrawal of blood from the inferior vena cava. Serum is separated from the blood and used to determine total and allergen specific levels of 1-E and IgG in the blood. A 21-gauge needle is inserted into the trachea and secured with a 3-0 silk suture. The lungs are lavaged via the tracheal needle with 3×1 ml of PBS. Lavage fluid is later used for morphological characterization of cells on cytospin slides after May-Grunwald Giemsa staining for characterization of cells by FACS analysis and for examination of cytokines levels by ELISA. The lungs are removed and inflated with 4% buffered formalin under pressure of 20 cm H$_2$O The tissues are embedded in paraffin and 2 to 3 µm sections are cut and stained with H&E for viewing by light microscopy the inflammatory changes in the peribronchial areas. The serum is collected for IgE level measurements.

Data is collected on an excel spreadsheet. The differences between groups are calculated with ANOVA test for the parametric measurements and with Kruskal Wallis test for the ordinal parameters (pathology score). A $p<0.05$ is considered significant.

Example 4

Animal Model

In the following, female, 8-9 week old BALB/c mice were used for the development of an asthma model. The experiment was divided into two parts:

In the first part establishment of rye grass pollen allergic mice model was achieved through intranasal sensitization and challenge with *Lolium perenne* pollen extract in a 21-day time period. In this part there were two groups of mice: asthmatic, which received both sensitization and challenge with *Lolium perenne* pollen extract and naïve which received both sensitization and challenge with PBS. Each group contained 3 mice.

In the second part all the mice were sensitized and challenged with *Lolium perenne* pollen extract for 21 days. As day 26, the mice were divided into two groups: asthma group which received a 15 minute inhalation of *Lolium perenne* pollen extract and the treatment group which received a 15 minute inhalation of *Lolium perenne* pollen extract mixed with OCAM. Each group contained 3 mice.

*Lolium perenne* (Perenial rye grass), Batch 021405105 obtained from Allergon A B, Sweden, was used for the preparation of an extract. Five grams of pollen were suspended in 50 ml phosphate buffered saline (PBS) and extracted by stirring at room temperature for 15 minutes. After centrifugation at 20000×g for 10 min at 4° C. the supernatant was kept and the content of soluble proteins was determined using the BCA reagent (Pierce).

Sensitization—Mice were anesthetized with isoflurane and then sensitized intranasally with 100 µg/animal of grass pollen soluble proteins in 50 µl PBS on days 0, 1, and 2.

Airway Challenge—Mice were anesthetized with isoflurane and challenged on days 14, 15, 18, and 19 intranasally with 25 µg grass pollen soluble proteins. Naïve mice were sensitized and challenged intranasally with PBS. The mice were then either sacrificed at clay 21 or given an additional 15-minute inhalation challenge of either grass pollen soluble proteins 4 mg/ml or grass pollen soluble proteins 4 mg/ml OCAM mixture (4 mg/ml pollen proteins and 13 mg/ml OCAM) at day 26 and sacrificed at day 29.

Analysis of Bronchoalveolar Lavage (BAL)—Bronchoalveolar lavage fluids (BALF) were obtained via cannulation of the exposed trachea, by infusion of 3×1 ml of PBS through a 21-gauge needle into the lungs, followed by aspiration of this fluid into a syringe. Aliquots were centrifuged, and supernatants were collected and stored at −80° C. for future cytokine analysis. Cell pellets were counted and subjected to cytospin, and the slides were stained May-Grunwald Giemsa and were characterized morphologically.

Sensitization and challenge with Rye grass pollen extract results in allergic lung inflammation of BALB/C mice—

Since there is no available model of Rye grass pollen allergic mice a mouse model was developed using one of the accepted methods. BALB/c mice were thus sensitized intranasally with 100 µg/animal of grass pollen proteins extract in 50 µl PBS on days 0, 1, and 2 and challenged on days 14, 15, 18, and 19 intranasally with 25 µg grass pollen soluble proteins. On day 21 mice were sacrificed and BALF were obtained and analyzed.

Figure 1A:
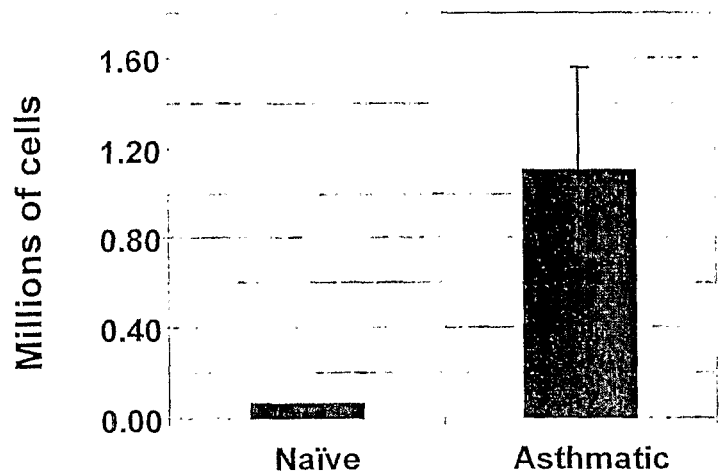
Figure 1B:
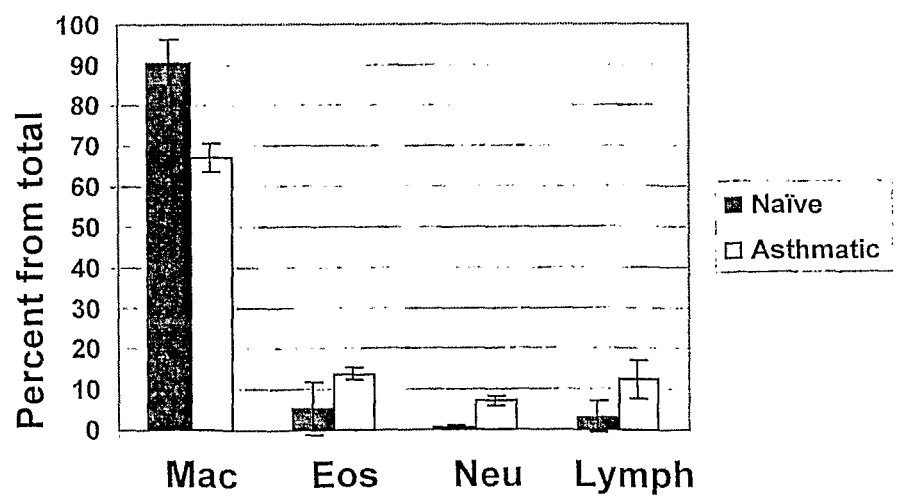

As FIG. 1A shows, the asthmatic animals that were treated with pollen proteins, showed an increase in their BALF cell counts compared to the naïve group that was treated with PBS, indicating the development of lung inflammation. Since the allergic reaction is characterized by Th2 mediated lung inflammation the nature of cells in the BALF was next evaluated by May-Grunwald staining. As FIG. 1B shows there was a significant increase in the recruitment of eosinophils to the lungs in the asthmatic mice compared with the naïve mice indicating that the inflammation was indeed of allergic nature.

Figure 1C:
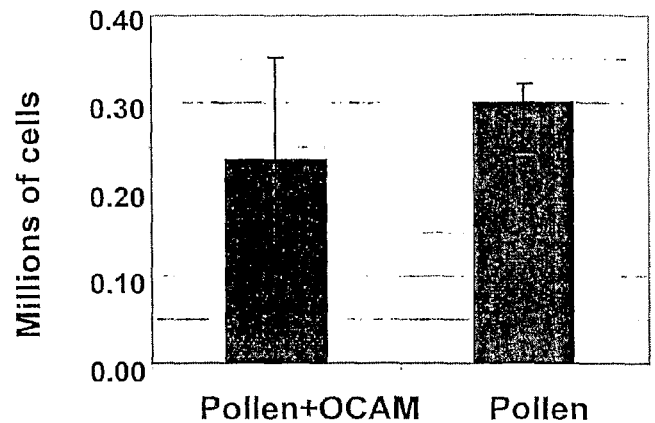
Figure 1D:
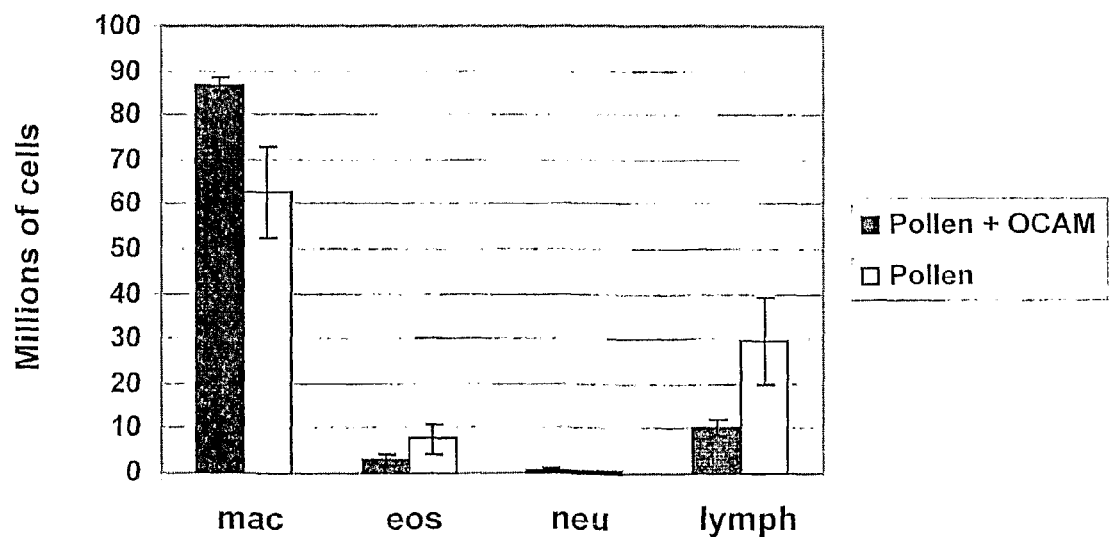

OCAM can attenuate the induction of allergic inflammation in asthmatic mice—It was next needed to verily whether OCAM could block the initiation of a secondary lung inflammation in the asthmatic mice. The asthmatic mice reached a peak of inflammation of the lungs at day 21 and were thus left untreated until day 26 in order to allow the inflammation to calm down. At day 26 the asthmatic mice were divided into two groups and both were given a challenge by inhalation. However, one group received a challenge of grass pollen protein extract only while the second group received an inhalation of OCAM grass pollen extract mixture. The mice were sacrificed 72 hours later and their cell counts and morphology were analyzed in the BALF. As can be seen in FIG. 1C the total number of cells was quite low when compared to the inflammation at day 21, with no significant difference between the two groups, indicating that the single challenge at day 26 induced only a weak inflammation. Examination of the nature of the cells in the BALF, however, showed a reduction in the percent of macrophages (the main cells in healthy mice) and an increase in the percent of eosinophils and lymphocytes in the pollen only group, indicating the induction of inflammation by the allergic challenge. Importantly, the change in all the parameters of inflammation that were just described was significantly lower in the group that received the OCAM and grass pollen protein mixture (FIG. 1D). This clearly and unambiguously indicated that the binding of pollen allergens to OCAM prevented them from inducing the allergic reaction.

In similar experiments, particles of chitosan are used in place of the oxidized cellulose.

Example 5

Determination of Allergy Blocking by OCAM in Rat Animal Model

The following is a basic protocol developed for determining the efficacy of the compositions and methods of the invention on animals. A person skilled in the art would appreciate that this protocol may be regarded of only one example and that other more specific or more generic models may be developed for the purpose.

In the following, male, Brown Norway rats, 3 weeks of age and weighing 150 grams each are used for an asthma model. Rats are divided into 3 treatment groups (naïve, asthma, and treatment groups), 10 rats in each group. Naïve rats are used as negative controls and are not sensitized. 20 rats are sensitized as described below. 10 rats are treated with OCAM inhalation before each allergen challenge (treatment group).

Grass pollen is used for the preparation of an extract. Five grams of pollen are suspended in 50 ml phosphate buffered saline (PBS) and extracted by stirring at room temperature for 15 minutes. After centrifugation at 20000×g for 10 min at 4° C. the supernatant is filtered through a 0.45-micron filter. The protein concentration of the grass pollen extract is determined using the BCA reagent (Pierce).

Induction of asthma—Brown Norway rats, 3 weeks old, weighing 150 grams each are sensitized at day 0 by subcutaneous injection of 1 mg of *Lolium perenne* (Rye grass) soluble proteins and 200 mg of aluminum hydroxide (Merck) in 0.9% (w/w) saline in a total volume of 1 mL, and intraperitoneal injection of 1 mL saline containing *Bordetella pertussis* ($6 \times 10^9$ heat killed organisms) (Pasteur Marieux, France). The animals are challenged every other day from day 14 until day 21 with repeated allergen (*Lolium perenne* proteins) inhalation 1 mg/ml.

Bronchoconstriction Measurements—Before and after every challenge bronchoconstriction is measured in unrestrained conscious rats using a method validated by (Hamelmann et al., 1997) and expressed as the enhanced pause (Penh), before and after allergen or allergen+OCAM challenge. Animals are placed in a whole-body plethysmograph. Analogue signals from the amplifier are converted to digital signals by AD card (LPM-16 National Instruments, Austin, Tex.). Software (System XA, model SFT 1810, Buxco Electronics) is used to analyze 10 breath signals and calculate the respiratory rate, and Penh. This %ΔPenh is used to compare the difference in bronchoconstriction between the treatment groups.

Bronchoalveolar Lavage (BAL)—BAL is performed 48 hours after the last challenge. Mice are anesthetized with I.P. injection of Ketamine/Xylazine (200 mg/kg) and sacrificed by bleeding from the abdominal aorta. The mice are than tracheotomized and incanulated through the trachea. BAL is performed with 5 ml of PBS in aliquots of 1 ml each time. The lavage fluid is collected in sterile tubes (Falcon) and placed immediately in ice. BAL is used for cell count and differential cell count (after May-Grunwald Giemsa staining) and for measurement of cytokines.

Pathology—Lungs are removed and fixed by inflation with paraformaldehyde at a pressure of 20 cm $H_2O$. The lung tissues are cut longitudinally in three, embedded in paraffin, randomly sliced and stained with eosin-hematoxylin for assessments of interstitial and peri-bronchial inflammation. Other slides are stained with Alcian blue and PAS for epithelial cell mucus metaplasia.

Example 6

Formulation of OCAM Suitable for Nasal Spray, Inhalation and Topical Cream

OCAM formulations for nasal spray, inhalation and topical cream are prepared based on common and acceptable ingredients. The stability of the formulations is tested in an accelerated stability study. OCAM allergen blocking will be determined by IgE-ELISA.

Example 7

Binding of Rye Grass Pollen Proteins to Microcrystalline Cellulose or to OCAM Prepared Therefrom Preparation of soluble pollen proteins—Pollen from Lolium perenne or *Lolium rigidum* (100 mg per sample) were dissolved in 1 ml of PBS. The pollen solvent mixture was rotated for 15 minutes after which point the pollen was separated from the supernatant by centrifugation.

Binding assay—Microcrystalline cellulose, KOH washed microcrystalline cellulose, OCAM or Barely beta-glucan CAS:P-BGBL (Megazyme, Ireland) were suspended in PBS alt a concentration of 20 mg/ml. A total of 5-20 mg polysaccharide/sample were precipitated in an eppendorf tube, resuspended in 450 µl of PBS, mixed with 200 µl of pollen supernatant and rotated for 1 hour. The particles were precipitated and the supernatant termed unbound fraction (UB) was collected and mixed 1/1 in sample application buffer (SAB). The cellulose particles pellets were then washed twice in PBS and resuspended in 30 µl SAB X2 (termed Bound (B) fraction). Total proteins (termed T) were made by diluting the pollen sup 1/4 with PBS and then mixing the diluted proteins 1/1 with SAB X2. All samples were boiled. Samples B, UB and T were loaded to and separated by 15% or gradient glycine gels and stained with either coomassie blue or silver stain. Indicated bands were excised from the gel and analyzed by LC-MS/MS.

Figures 2A, 2B:
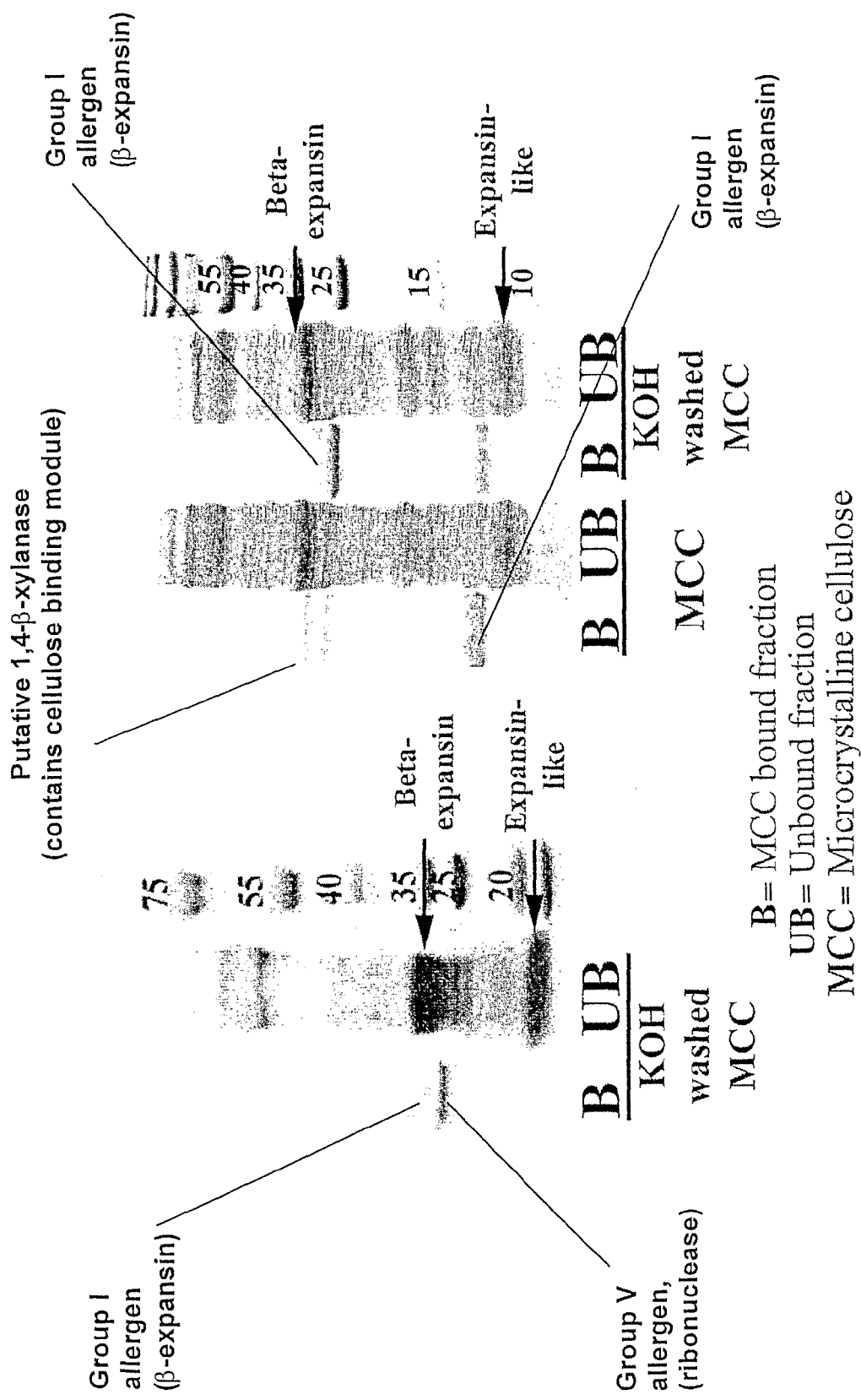
Figure 4:
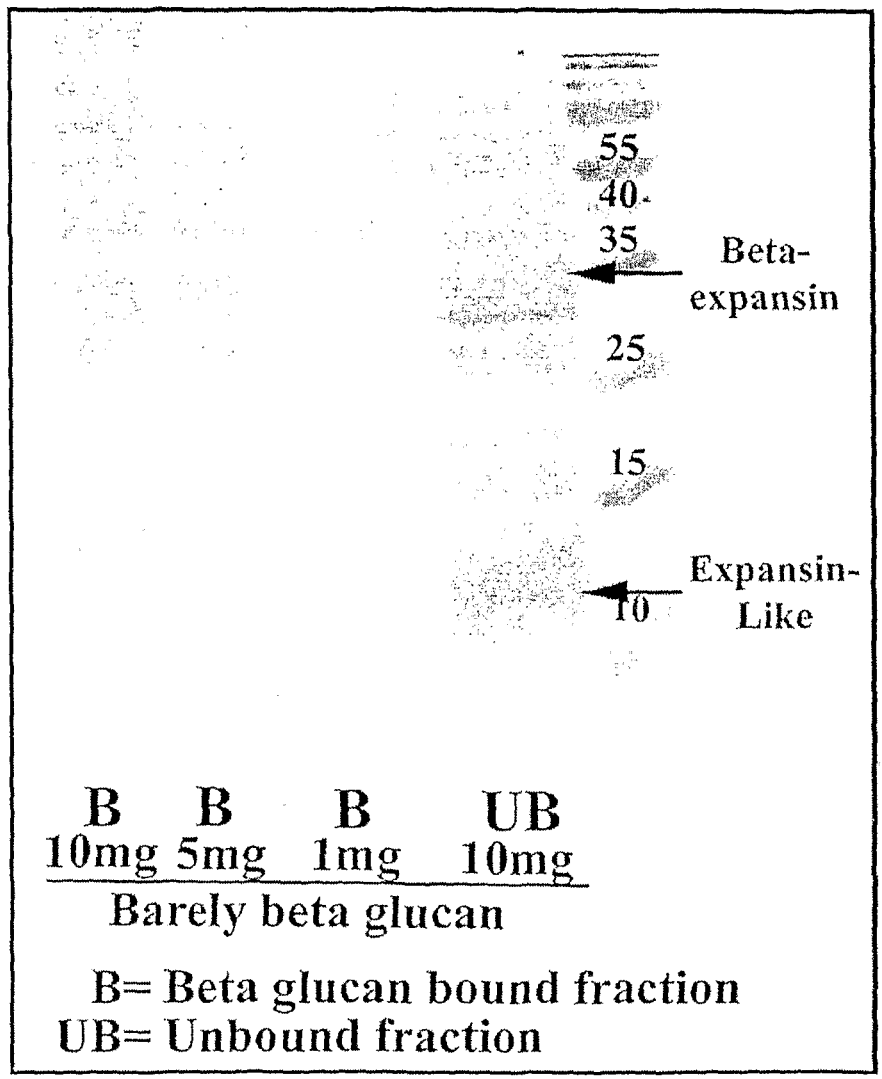

As FIGS. 2-4 show:

1. microcrystalline cellulose, OCAM (oxidized cellulose made from microcrystalline cellulose) and beta-glucan were able to bind a portion of the pollen proteins;

2. sequencing of the major microcrystalline bound proteins revealed mostly allergens including the expansin family; and 3. oxidation of microcrystalline cellulose dramatically increased its pollen-protein binding capacity.

Unlike microcrystalline cellulose, OCAM bound most of the pollen proteins, which can be observed from the massive reduction of proteins in the unbound fraction, Most of the different pollen proteins were found in the OCAM bound fraction.

The invention claimed is:

1. A method for treatment of an allergy, said method comprising administering to a subject in need thereof a pharmaceutical composition comprising an anti-allergy agent consisting of oxidized cellulose.

2. The method according to claim 1, wherein said oxidized cellulose is a salt or derivative of the oxidized cellulose.

3. The method according to claim 2, wherein said oxidized cellulose or salt or derivative thereof is in a form of solid particulates.

4. The method according to claim 3, wherein said solid particulates are in an amorphous form.

5. The method according to claim 3, wherein said solid particulates are microparticles.

6. The method according to claim 3, wherein said solid particulates have average diameter of between 0.01 and 100 microns.

7. The method according to claim 1, wherein said oxidized cellulose derivative is a drug derivative.

8. The method according to claim 1, wherein said allergy is selected from the group consisting of urticaria, angioedema, and atopic dermatitis.

9. The method according to claim 1, formulated for topical, oral, aerosol, intranasal, intraocular, parenteral, subcutaneous, intravenous, intramuscular, interperitoneal, rectal, or vaginal administration.

10. The method according to claim 9, being selected from a topical formulation, an intranasal formulation, and an intraocular formulation.

11. The method according to claim 1, wherein said pharmaceutical composition comprising oxidized cellulose particles having an averaged diameter of between about 0.01 and 100 microns.

12. A method for delaying onset or lessening severity of an allergy, said method comprising administering to a subject an effective amount of an anti-allergy agent consisting of oxidized cellulose.

13. The method according to claim 5, wherein the microparticles having an average diameter in a range of 0.1 to 10 microns.

14. A method for treating an allergy, said method comprising administering to a subject in need thereof a pharmaceutical composition comprising an anti-allergy agent consisting of oxidized cellulose, wherein the oxidized cellulose is a rigid, unbranched, long chain polymer, consisting of 3,000 to 5,000 glucose residues in β-(1,4) linkage, having at least part or all of hydroxy methylene (exocyclic —$CH_2OH$) groups oxidized to carboxylic acid (—COOH) groups, charged carboxylate groups (—COO), or in a derivatized form having some or all of oxidized groups in a form (—COOR);

wherein the charged carboxylate groups is in a form of —COOX, wherein X is a monovalent, divalent or multivalent metal ion of alkali and/or alkaline metal ions;

wherein the carboxylic acid (—COOH) groups has a percent weight in a range of 3 to 25% of a total weight of the oxidized cellulose;

wherein the derivatized form (—COOR) R is an organic radical selected from substituted or unsubstituted C1 to C20 alkyl, cycloalkyl, alkylene or cycloalkylene; substituted or unsubstituted C6 to C12 aryl or arylene; substituted or unsubstituted C5 to C12 heteroarly or heteroarylene, C2 to C20 alkenyl, alkenylene, cycloalkenyl or cycloakenylene; wherein each of said groups may be substituted by one or more organic or inorganic atom or groups including halogen, Br, Cl, I, F, nitro, amines, alkys, aryls, wherein the heteroarly or heteroarylene has at least one heteroatom selected from N, O, S and combinations thereof.

15. The method according to claim 1, wherein said allergy is an allergic skin disease.

16. The method of claim 15 wherein the allergic skin disease is selected from the group consisting of allergic urticaria, allergic angioedema, and allergic atopic dermatitis.

* * * * *